United States Patent [19]

Kaletzky

[11] Patent Number: 4,586,499

[45] Date of Patent: May 6, 1986

[54] SURGICAL BANDAGE DISPOSABLE COUPLING DEVICE

[76] Inventor: Esther Kaletzky, 40 Waterside Plz., New York, N.Y. 10010

[21] Appl. No.: 591,273

[22] Filed: Mar. 19, 1984

[51] Int. Cl.[4] .................... A61F 13/00; A44B 21/00
[52] U.S. Cl. .................................. 128/171; 128/346; 24/336; 24/346; 24/643; 24/652
[58] Field of Search .................. 128/171, 346; 24/336, 24/346, 643, 652

[56] References Cited

U.S. PATENT DOCUMENTS

| 1,234,125 | 7/1917 | Bowman | 24/346 |
| 3,100,324 | 8/1963 | Tutino et al. | 24/137 |
| 3,857,140 | 12/1974 | Leveen | 128/170 |
| 3,863,301 | 2/1975 | Leveen | 128/171 |

FOREIGN PATENT DOCUMENTS

| 175068 | 2/1917 | Canada | 24/336 |
| 501803 | 4/1954 | Canada | 24/137 |
| 372518 | 4/1907 | France | 24/336 |
| 516006 | 4/1921 | France | 24/336 |
| 1996 | of 1902 | United Kingdom | 24/336 |
| 7708 | of 1909 | United Kingdom | 24/336 |

Primary Examiner—John Doll
Assistant Examiner—O. Chaudhuri
Attorney, Agent, or Firm—Howard C. Miskin

[57] ABSTRACT

An arrangement for supporting a limb wound bandage includes a waist belt and couplers extending from the belt to the bandage, each coupler including a pair of clamp jaws with confronting intermeshing ridges and valleys sandwiching and gripping the bandage upper border. Bands extend upwardly from each pair of jaws and are superimposed and joined at their tops and engage a connector which in turn directly or indirectly engages the belt. A locking slide member slidably engages the superimposed bands and includes depending tongues slidably engaging the clamp jaw outside faces to releasably lock the clamp jaws in closed position.

11 Claims, 6 Drawing Figures

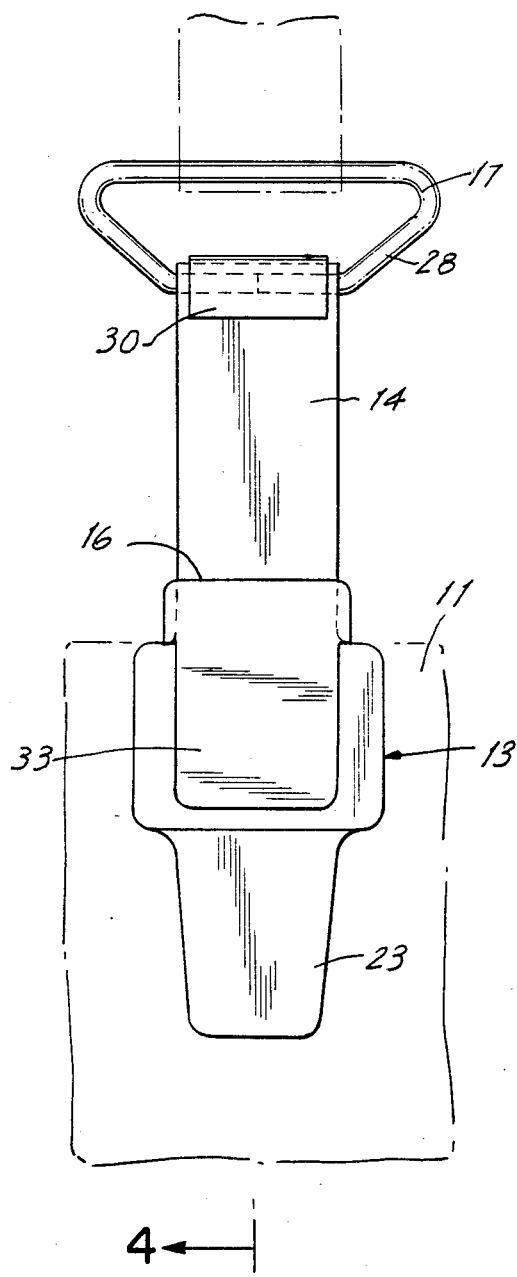
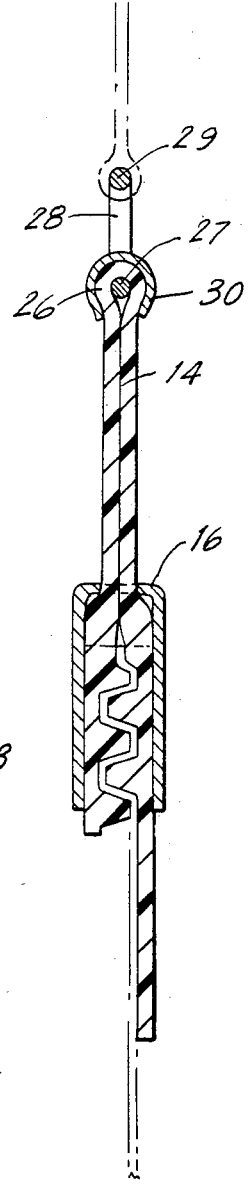
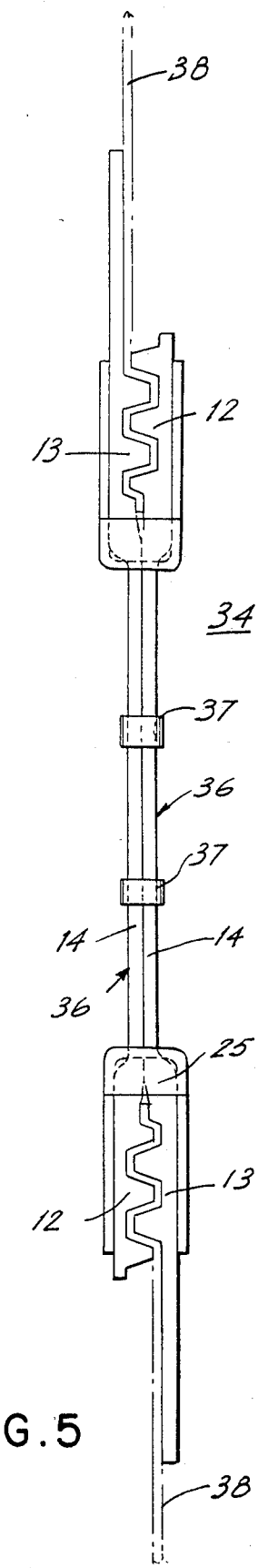
FIG. 3
FIG. 4
FIG. 5

SURGICAL BANDAGE DISPOSABLE COUPLING DEVICE

BACKGROUND OF THE INVENTION

The present invention relates generally to improvements in medically oriented devices and more particularly to an improved device for the firm and hygienic fixing and supporting of heavy orthopedic bandages covering surgically clean dressings on wounds, incisions and skin punctures, particularly on tapering portions of the patient's body, such as limbs and it also relates to an improved disposable, flat, light weight grip-holder mounted on adjustable and selectively distributed suspension supports.

The importance and usefulness of secure bandaging in the medical field, particularly during recovery following surgery, serious accidents and burns is quite obvious. The conventional technique of using strong surgical sticky tape for attaching heavy bandages directly to the skin surface has serious disadvantages and possesses substantial risks of skin damage and originating new wounds around the bandage as quickly as in a few hours upon its application, which in turn may lead to undesirable secondary infections in the area adjacent to the main wounds.

Relatively loose bandaging is usually recommended during medical treatment of injured limbs to provide for normal blood circulation and to minimize the danger of blood clot formation or other circulatory complications. In addition, a requirement for limited ventilation of the wound may be imposed to assure the patient's comfort by providing for an escape of perspiration and some flow of oxygen to the wound and thus to promote its more rapid healing.

On the other hand, if the above requirements are fulfilled a pronounced tendency of the heavy, relatively loose bandage to slip away together with the sterile protective dressing from the larger cross-sections of tapering body parts is often observed, particularly during the patient's motion because movement of limbs are now commonly prescribed to be performed as soon as possible after most operations and during medical treatment.

If external bandages become insecure the purpose of a sterile protective dressing may be defeated as the open wound or incision becomes partially or fully exposed to dangerous ambient infections, as well as other possible harmful post-operative effects. As it quite often happens in orthopedic practice or other medical treatment stitching may not always be applied and wounds are left open to heal in a natural way to provide for drainage of puss or subsequent removal of debris from the wound. Thus, complete healing normally takes a month or so, the patient is usually discharged from the hospital before the final healing and allowed to pursue normal activities; then, the necessity of securing a proper protection of the wounds becomes even more acute, particularly for people with hazardous environmental occupations.

SUMMARY OF THE INVENTION

It is the principal object of the present invention to provide a secure and sterile orthopedic bandage support and carrying which can be applied and promptly fitted to tapering portions of the patient's body without unduly confining or irritating the body during rest, sleep or motion.

Also an object of this invention is to provide improved, inexpensive, sterile and highly versatile orthopedic bandage supporting means adapted to be easily and quickly applied, removed and readjusted as required.

Another object of the present invention is to provide an improved adjustable bandage carrier device which could be operated by surgeons, attending physicians or nurses promptly and with ease without risks to the patients thereby permitting a normal blood circulation and some ventilation while the general environment of the injury or wound remains well protected.

A further object of the present invention is to provide a versatile supporting and carrying device well adapted to the injured area of the body and readily accommodating adjustments in accordance with medical requirements and comfort conditions of the patient during rest, sleep or movements.

Still another object of the present invention is a provision of a resilient engagable and disengagable bandage grip-holding device fixed in various positions on the enshrouded area including a plurality of flat single or twin snap-on grip-holders distributed thereabout in a prescribed manner to secure the desired degree of bandage support and tightness.

A still further object of the present invention is to assure a rapid application of the supporting device to the area required and at the same time to preserve the sanitary conditions obligatory for medical, surgical and post-operative care without damaging or tearing the bandage.

The above and other more specific objects of the present invention will appear upon reading the following description taken in conjunction with the attached drawings which relate to the preferred embodiment thereof.

The improved orthopedic bandage carrier in accordance with the present invention comprises a combination of a plurality of disposable snap-on grip-holders catching and holding in position several layers of the stretchable resilient "ACE" type bandage used for external protection of surgically clean dressing materials, including sterile curity gauze, sponges and sterile composite paddings applied directly to the patient's wounds, being firmly attached to a number of longitudinally and circumferencially adjustable suspenders positioned on loops and sliding along secondary supporting means adapted to be worn around the waist such as belts, waistbands, shoulder holders or straps worn on the patient's shoulders or a combination of them suitable for particular requirements.

The ridges of the grip-holder jaws are preferably formed of an elastomer, such as rubber, spandex or the like having a strong cloth base skin and may have two, three or more staggered teeth on its gripping surfaces and flat sliding slip-socket tightening or locking clamps are made of metal or firm plastic and should be as thin and light as possible.

The improved orthopedic bandage carrier is hygienic, highly reliable and convenient, can be easily and rapidly applied to a wound bandage and taken off and is of great versatility and adaptability.

BRIEF DESCRIPTION OF THE DRAWINGS

FIG. 3 is a front elevational view thereof;

FIG. 4 is a sectional view taken along line 4—4 in FIG. 3;

FIG. 5 is a side elevational view of another embodiment of the present invention.

DESCRIPTION OF THE PREFERRED EMBODIMENT

Figure 1:
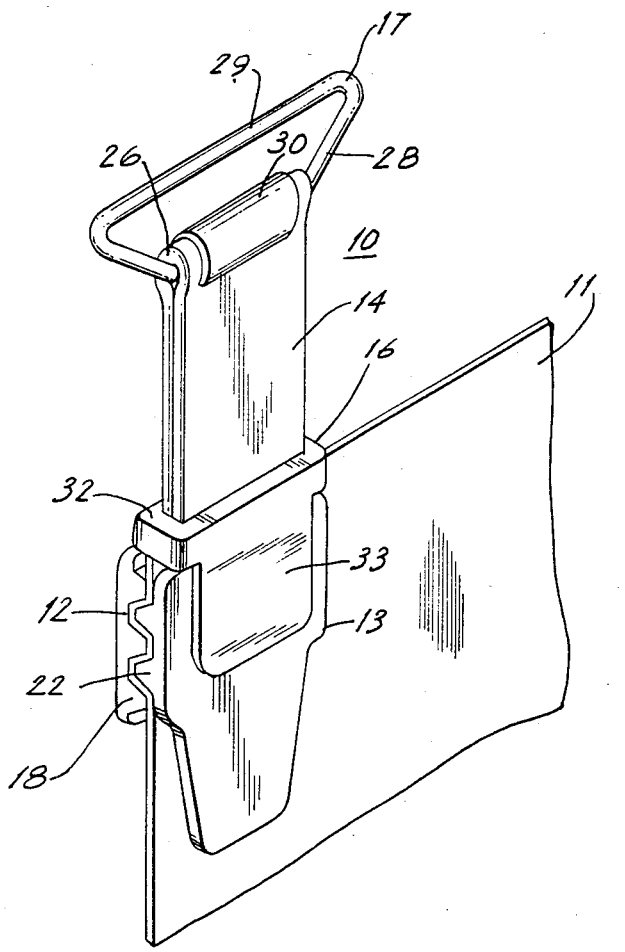
FIG. 1 is a front perspective view of a web coupling device embodying the present invention, illustrated in a web clamping position.
Figure 2:
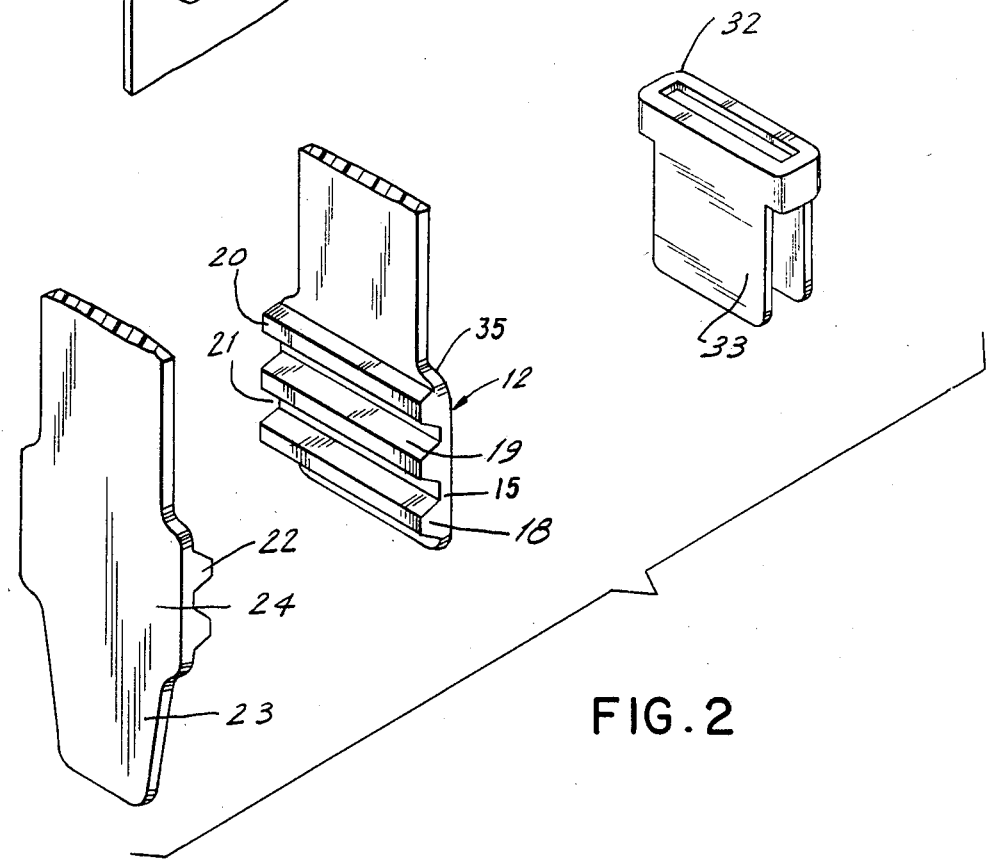
FIG. 2 is a fragmentary exploded perspective view thereof.

Referring now to the drawings, particularly FIGS. 1 to 4 thereof which illustrate a preferred embodiment of the present invention, the reference numeral 10 generally designates the improved coupling device shown attached to and supporting a web 11 which may be a medical or surgical bandage or the like. The coupling device 10 comprises a pair of clamp jaws 12 and 13, a pair of superimposed suspension bands 14, a clamp jaw locking member 16 and a connector 17.

The clamp jaws 12 and 13 are integrally formed with respective bands 14 which are integrally joined at their upper ends and are formed of a suitable flexible, relatively soft preferably elastomeric material such a polyolefin, polyvinyl chloride or other synthetic polymer or an elastomer. The clamp jaw and band unit may be produced by injection molding or other suitable process.

The clamp jaw 12 includes a rectangular back panel 15 with a smooth outer face and has formed on its inner face longitudinally spaced transverse ridges 18 of trapezoidal transverse cross section with flat smooth outwardly converging side faces 19 and flat apices 20. Separating ridges 18 are valleys 21 likewise of trapezoidal transverse section similar to that but slightly wider than of ridges 18. The upper outer face of jaw 12 terminates in a transverse shoulder 35 and is integrally medially joined to one end of band 14 which is of lesser width than clamp jaw 12.

Clamp jaw 13 is integrally joined to the other end of band 14 and is similar in construction to clamp jaw 12 and includes a pair of longitudinally spaced ridges 22 of trapezoidal transverse cross section staggered relative to the three ridges 18 of clamp jaw 12 so as to be engagable with valleys 21. A trapezoidal tongue 23 medially depends from and is coplanar with the back panel 24 of jaw member 13.

The band 14 is folded about its medial transverse axis into superimposed position, forming a transverse loop 26 at its folded portion. The lower cross bar 27 of connector 17 traverses loop 26 and diverging arms 28 extend from cross bar 27 and are joined at their outer ends by an outer cross bar 29. The band loop 26 is secured to cross bar 27 by a resilient split sleeve 30 partially encircling loop 26 and the coaxial cross bar 27.

The locking member 16 is light and thin and is formed of a relatively rigid material such as a suitable metal and comprises a rectangular slide or collar 32 including a flat frame and a depending peripheral skirt wall 25 and longitudinally slidably engaging superimposed bands 14. Medially depending from the opposite long sides of the skirt wall 25 of collar 32 is a pair of parallel rectangular locking panels or tongues 33 of lesser width than jaws 12 and 13. Tongues 33 are slidably engagable with the outer faces of clamp jaws 12 and 13 when the latter are in relatively closed or contracted condition.

In attaching coupling device 10 to a bandage or other web 11, locking member 16 is slid upwardly along bands 14 until tongues 33 release clamp jaws 12 and 13. The clamp jaws are then separated and positioned along opposite faces of the border of web 11 and then pressed together to bring the valleys and ridges of the jaw clamp face into engagement with the web tightly sandwiched between the jaws mating and confronting faces. The clamp jaws are then locked in their closed web clamping position by sliding locking member 16 downwardly until the frame portion thereof bears on the upper ridges of jaws 12, 13 to bring tongues 33 into locking engagement with the outside faces of jaw panels 15 and 24. The coupling device may be attached to any desired support by means of connector 17.

Another embodiment of the present invention is shown in FIG. 5 of the drawing and differs from that first described in that a pair of band and jaw member pairs are employed in coupling two webs, the connector 17 being obviated.

Specifically, the modified device 34 includes a pair of similarly shaped coupling sections 36 each being similar in structure to the coupling section previously described including the clamp jaws 12 and 13 and band 14. In the subject arrangement the bands 14 extend longitudinally and are superimposed along most of their lengths and so retained by a pair of longitudinally spaced retainer collars 37. The jaws 12 and 13 of each section 36 are in mating confrontation with the jaws 12 and 13 of the other section 13. Slidably engaging each of the end portions of the superimposed bands 14 is a clamp jaw locking member 16.

In coupling two webs 38 with the coupling device 34 a border of each web 38 is clamped between a pair of jaws 12 and 13 which are then locked in their clamp position by locking member 16 in the manner described in connection with the first embodiment.

Figure 6:
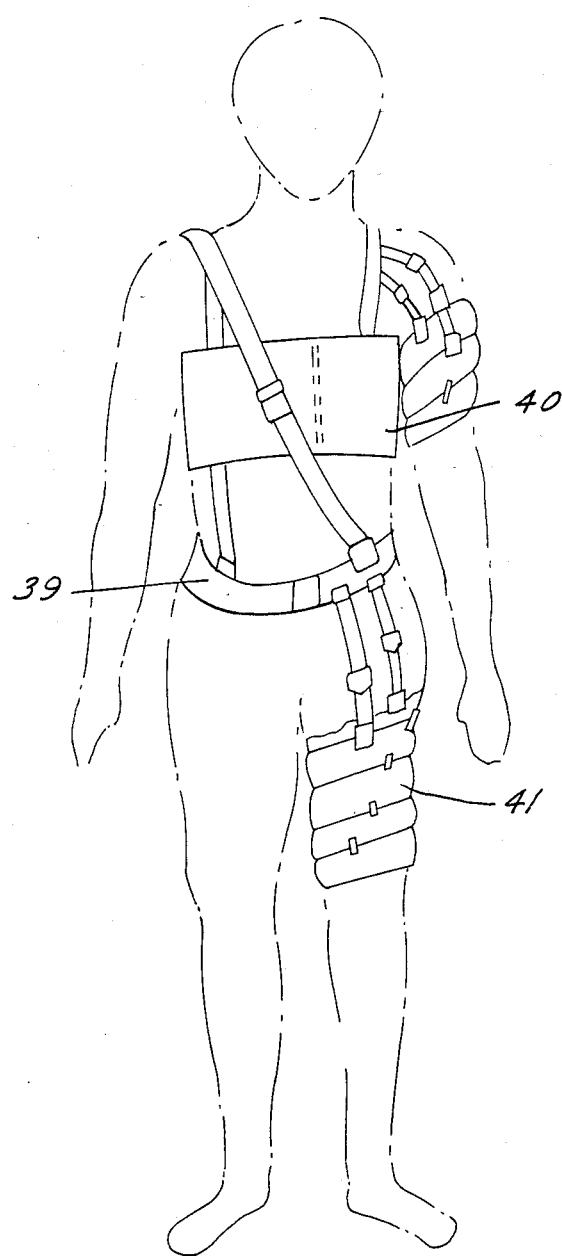
FIG. 6 is a fragmentary view of a subject having applied devices in accordance with the present invention.

An example of the application of the improved web coupling device is shown in FIG. 6 as applied to the support of a thigh encircling or wound bandage. An adjustable belt 39 is worn about the waist of a subject or patient 40 and a bandage such as an elastic ACE bandage 41 or other web encircles or is wound around the subjects thigh. One or more coupling devices 10 or 34 in accordance with the present invention have their lower clamp jaws 12, 13 sandwiching and clamping the upper border of bandage 41 and the upper connectors 29 or 12, 13 are attached to the belt 39. Longitudinally adjustable loops may be provided on belt 39 to which the coupling member connectors may be attached.

While the description has been directed to medical uses, the disclosure may be used for other applications as well.

While there have been described and illustrated preferred embodiments of the present invention, it is apparent that numerous alterations, omissions and additions may be made without departing from the spirit thereof.

I claim:

1. A web coupling device comprising a first pair of first clamp jaws defining soft resilient panels having opposing confronting inner gripping faces and outer faces in backing registry with respective of said inner faces and being relatively movable between a closed clamp position with said gripping faces in non-slipping engagement with a web and a separated web release position, a flexible band extending longitudinally from at least one of said jaw panels, a locking member including a slide member slidably engaging said band and including a pair of spaced confronting relatively rigid locking sections projecting longitudinally from and being longitudinally movable with said slide member between a lock position with said slide member above said outer faces and with said locking sections superimposed on and engaging said jaw panel outer faces backing said inner faces to releasably retain said jaws in their lock position sandwiching a web between said panel inner faces and a release position with said locking sections disengaged and longitudinally displaced from said jaw panel outer faces to permit the separation of said jaws, and a connector attached to said band.

2. The web coupling device of claim 1 wherein one of said bands extends from each of said jaws, said bands being in substantially superimposed position and said slide member slidably engages said superimposed bands.

3. The web coupling device of claim 1 wherein said bands are mutually joined in an area longitudinally spaced from said jaws.

4. The web coupling device of claim 1 wherein said bands are integrally joined at their ends remote from said jaws.

5. The web coupling device of claim 1 wherein said slide member and locking sections are integrally formed of a relatively rigid material.

6. The web coupling device of claim 5 wherein said slide member comprises a rectangular collar encircling said bands and opposite tongues defining said locking sections depending from opposite long sides of said collar.

7. The web coupling device of claim 1 wherein each of said jaw gripping faces includes longitudinally spaced laterally extending ridges with outwardly converging opposite faces separated by valleys of cross-sections similar to that of said ridges whereby the ridges of each jaw face is matingly engagable with the valleys of the opposite jaw face.

8. The web coupling device of claim 4 wherein said connector comprises a coupling ring engaging the loop defining joined ends of said bands.

9. The web coupling device of claim 2 wherein said connector comprises a second pair of clamp jaws joined to the ends of said bands and a second slide member slidably engaging said bands and having locking sections longitudinally movable therewith between positions respectively embracing and releasing said second jaw members.

10. In combination with the coupling device of claim 1 an upper band encircling and secured to a subject's waist, a web encircling a portion of the subject below said upper band, the jaws of said coupling device clamping a border of said web and being locked thereto by said slide member being in its locked position and means coupling said connector to said upper band.

11. The web coupling device of claim 1 wherein said band is narrower than said respective jaw panel and is delineated therefrom by a transversely extending shoulder and said sliding member comprises a collar slidably engaging said band and restricted in its movement toward said respective jaw by said shoulder.

* * * * *